US011691037B2

United States Patent
Ishida et al.

(10) Patent No.: US 11,691,037 B2
(45) Date of Patent: Jul. 4, 2023

(54) METHOD FOR FORMING COATING ON SKIN SURFACE

(71) Applicant: KAO CORPORATION, Tokyo (JP)

(72) Inventors: Kaori Ishida, Utsunomiya (JP); Takehiko Tohjo, Utsunomiya (JP); Kenta Mukai, Utsunomiya (JP); Yuki Otorii, Katsushika-ku (JP)

(73) Assignee: KAO CORPORATION, Tokyo (JP)

( * ) Notice: Subject to any disclaimer, the term of this patent is extended or adjusted under 35 U.S.C. 154(b) by 808 days.

(21) Appl. No.: 16/606,314

(22) PCT Filed: Apr. 19, 2018

(86) PCT No.: PCT/JP2018/016185
§ 371 (c)(1),
(2) Date: Oct. 18, 2019

(87) PCT Pub. No.: WO2018/194131
PCT Pub. Date: Oct. 25, 2018

(65) Prior Publication Data
US 2021/0228457 A1 Jul. 29, 2021

(30) Foreign Application Priority Data

Apr. 19, 2017 (JP) ................................ 2017-082984

(51) Int. Cl.
| | | |
|---|---|---|
| *A61Q 19/00* | (2006.01) | |
| *A61K 8/02* | (2006.01) | |
| *A61K 8/33* | (2006.01) | |
| *A61K 8/891* | (2006.01) | |
| *D06M 13/02* | (2006.01) | |
| *D06M 13/144* | (2006.01) | |
| *D06M 13/224* | (2006.01) | |
| *A61K 8/30* | (2006.01) | |

(52) U.S. Cl.
CPC .............. *A61Q 19/00* (2013.01); *A61K 8/027* (2013.01); *A61K 8/0208* (2013.01); *A61K 8/30* (2013.01); *A61K 8/33* (2013.01); *A61K 8/891* (2013.01); *D06M 13/02* (2013.01); *D06M 13/144* (2013.01); *D06M 13/224* (2013.01); *A61K 2800/00* (2013.01); *A61K 2800/262* (2013.01); *A61K 2800/88* (2013.01); *D10B 2509/00* (2013.01)

(58) Field of Classification Search
CPC .................. A61Q 19/00; A61K 8/208
See application file for complete search history.

(56) References Cited

U.S. PATENT DOCUMENTS

| | | | | | |
|---|---|---|---|---|---|
| 5,849,834 | A | * | 12/1998 | Matsuzaki | ............. A61Q 19/00 526/240 |
| 2011/0256397 | A1 | | 10/2011 | Tojo et al. | |
| 2013/0125912 | A1 | | 5/2013 | Tojo et al. | |
| 2013/0142852 | A1 | | 6/2013 | Tojo et al. | |
| 2019/0059551 | A1 | | 2/2019 | Amari et al. | |
| 2019/0350825 | A1 | | 11/2019 | Uchiyama et al. | |

FOREIGN PATENT DOCUMENTS

| | | | |
|---|---|---|---|
| CN | 102245378 | A | 11/2011 |
| CN | 102958505 | A | 3/2013 |
| EP | 2 371 528 | A1 | 10/2011 |
| EP | 2 589 693 | A1 | 5/2013 |
| EP | 3 545 941 | A1 | 10/2019 |
| JP | 2005-290610 | A | 10/2005 |
| JP | 2008-179629 | A | 8/2008 |
| JP | 2010-167780 | A | 8/2010 |
| JP | 2011-132633 | A | 7/2011 |
| JP | 2012-12339 | A | 1/2012 |
| JP | 2013-28552 | A | 2/2013 |
| JP | 2013-119676 | A | 6/2013 |
| JP | 2013-241360 | A | 12/2013 |
| JP | 2015-113293 | A | 6/2015 |
| JP | 2015-209393 | A | 11/2015 |
| JP | 2017-78063 | A | 4/2017 |
| TW | I358484 | B | 2/2012 |
| WO | WO 2010/074213 | A1 | 7/2010 |

OTHER PUBLICATIONS

Xunzai, N., et al., "Paper Manufacturing Technology", China Light Industry Press Ltd., pp. 361-362, Sep. 30, 1999 with a machine generated English summary (concise explanation).
Extended European Search Report dated Nov. 20, 2020 in European Patent Application No. 18788001.8, 11 pages.
Anonymous: "Wrinkle Essence", Database GNPD[Online] MINTEL; Oct. 27, 2008, XP055748996, retrieved from the internet: www.gnpd.com, Database accession No. 986826, 4 pages.
International Search Report dated Jul. 24, 2018 in PCT/JP2018/016185 filed on Apr. 19, 2018.
Zong Y., et al., "Textile Materials Science (Fangzhi Cailiao Xue)", 2nd Edition, Donghua University Press, p. 114. Jun. 2013 (with English Abstract (Concise explanation) generated by machine), 7 total pages.

\* cited by examiner

*Primary Examiner* — Gina C Justice
(74) *Attorney, Agent, or Firm* — Oblon, McClelland, Maier & Neustadt, L.L.P.

(57) ABSTRACT

A method for forming a coating on a skin surface using a nanofiber sheet, the method including: (1) applying to the skin a sheet transparentizing agent containing 2 mass % or more of one or more oil agent; and (2) transferring a white nanofiber sheet mainly composed of a water-insoluble polymer to the skin after (1), where the transferred white nanofiber sheet becomes transparent and the coating is a transparent coating through which the skin is visible.

12 Claims, 1 Drawing Sheet

“METHOD FOR FORMING COATING ON SKIN SURFACE”

FIELD OF THE INVENTION

The present invention relates to a method for forming a coating on a skin surface.

BACKGROUND OF THE INVENTION

Sheets composed of nanofibers have been applied not only to fabrics and composite materials, but also to medical fields and cosmetic fields (Patent Literatures 1 and 2). As applications in the field of cosmetics, a cosmetic sheet in which a cosmetic is held in a network structure composed of nanofibers (Patent Literature 2), a cosmetic sheet in which a colored pigment is contained in a nanofiber sheet (Patent Literature 3), and a method for adhering a nanofiber sheet (Patent Literature 4) are known.

(Patent Literature 1) JP-A-2005-290610
(Patent Literature 2) JP-A-2008-179629
(Patent Literature 3) JP-A-2010-167780
(Patent Literature 4) JP-A-2012-12339

SUMMARY OF THE INVENTION

The present invention provides a method for forming a coating on a skin surface using a nanofiber sheet, the method comprising:

(1) Step (1) of applying to the skin a sheet transparentizing agent comprising 2 mass % or more of one or more oil agents; and (2) Step (2) of transferring a white nanofiber sheet mainly composed of a water-insoluble polymer to the skin after Step (1).

The present invention further relates to a transparent or translucent patch material comprising a combination of a sheet composed of fibers and a sheet transparentizing agent for forming a transparent or translucent coating on a skin surface, wherein the sheet is mainly composed of a water-insoluble polymer, the thickness of the fibers constituting the sheet is 10 nm or more and 1,500 nm or less in equivalent circle diameter, the thickness of the sheet is from 100 nm to 500 µm, and the L value is 80 or more and 100 or less, the sheet transparentizing agent comprises 5 mass % or more and 100 mass % or less of an oil agent comprising one or more selected from the group consisting of a hydrocarbon oil, an ester oil, and a higher alcohol, and the total amount P of the content of the hydrocarbon oil, the ester oil, and the higher alcohol in the oil agent is 50 mass % or more. In this patch material, the sheet is preferably a nanofiber sheet.

DETAILED DESCRIPTION OF THE INVENTION

Figure 1:
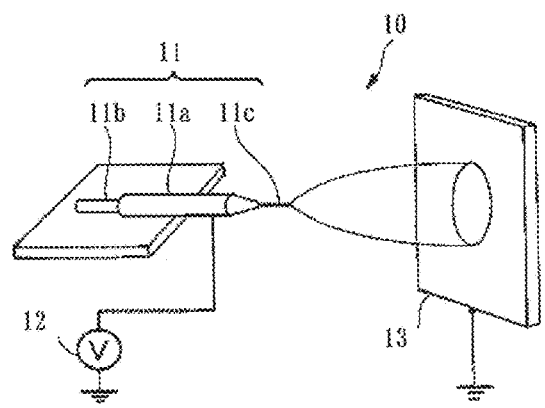
FIG. 1 is a schematic diagram showing a configuration of a device for manufacturing a nanofiber sheet used in the present invention.

However, among the conventional cosmetic nanofiber sheets, the sheet disclosed in Patent Literature 2 has an issue that a large amount of cosmetic component may not be held because the cosmetic component is mixed in the polymer solution to be electrospun, and the sheet is liable to be deteriorated. In addition, the nanofiber sheet containing the colored pigment, may be difficult to adhere to the skin, and it does not serve to forming a transparent coating that takes advantage of the color of the skin.

Thus, the present invention relates to a process for forming a transparent coating that is highly adherent to the skin and through which the skin is visible, and for maintaining the transparency of the obtained coating.

The present inventors have extensively investigated on methods for forming a nanofiber sheet on the skin, and have surprisingly found that if a composition containing an oil agent is applied in advance to the skin to which the nanofiber sheet is to be transferred and then a white nanofiber sheet containing a water-insoluble polymer as a main component is transferred, the adhered nanofiber sheet becomes transparent, thereby remarkably improving the adhesivity to the skin, to complete the present invention.

According to the method of the present invention, the adhesivity of the nanofiber sheet transferred to the skin is remarkably improved, and the transparency of the obtained coating is improved, so that the excellent transparency of the coating can be maintained.

The method for forming a coating on a skin surface using a nanofiber sheet of the present invention, comprises the following steps (1) and (2):

(1) Step (1) of applying to the skin a sheet transparentizing agent comprising 2 mass % or more of one or more oil agents; and (2) Step (2) of transferring a white nanofiber sheet mainly composed of a water-insoluble polymer to the skin after Step (1).

The sheet transparentizing agent used in Step (1) comprises one or more oil agents in a content of 2 mass % or more and 100 mass % or less. The content of the oil agent is preferably 3 mass % or more, more preferably 5 mass % or more, even more preferably 8 mass % or more, and the upper limit of the content of the oil agent is preferably 100 mass %, from the viewpoint of adhesivity of the nanofiber sheet to the skin and persistence of the transparent appearance. When the sheet transparentizing agent contains water, a water-soluble polymer, an active ingredient, or the like, the content of the oil agent in the sheet transparentizing agent is preferably 85 mass % or less, more preferably 75 mass % or less, and further more preferably 65 mass % or less.

The oil agent used in the sheet transparentizing agent may be an oil agent in a solid or paste state at 20° C., an oil agent in a liquid state at 20° C., or a mixture thereof.

Examples of the oil agent include a hydrocarbon oil, an ester oil, a higher alcohol, an ether oil, a silicone oil, and the like, and one or more selected from these oil agents can be used in combination. From the viewpoint of feel to the skin, it is preferable that the content of one or more selected from the group consisting of a hydrocarbon oil, an ester oil, and a higher alcohol be the content of the oil agent.

When a silicone oil or an ether oil is contained, the total amount S of these oil agents is preferably lower than the total amount P of the content of the hydrocarbon oil, the ester oil, and the higher alcohol, from the viewpoint of maintaining transparency for a long period and of improving the adhesivity of the nanofiber sheet, and the total amount S to the total amount P is more preferably 30 mass % or less, more preferably 10 mass % or less, and may not be contained. The total amount of the content of the silicone oil and ether oil in the sheet transparentizing agent is preferably 15 mass % or less, more preferably 10 mass % or less, and further more preferably 5 mass % or less, from the viewpoint of maintaining transparency for a long period and of improving adhesivity.

Among these, from the viewpoint of improving the adhesivity between the skin and the sheet and of preventing the sheet from slipping from the skin, it is more preferable to contain at least one or more selected from the group consisting of a hydrocarbon oil and an ester oil. In addition, it is preferable to use a combination of an oil agent in a liquid state at 20° C. and an oil agent in a solid or semi-solid state at 20° C.

The oil agent may also contain a volatile oil agent, but from the viewpoint of maintaining adhesivity to the skin and transparency of the sheet, the ratio of the volatile oil agent to the total oil agent is preferably less than 50 mass %, more preferably 30 mass % or less, further more preferably 10 mass % or less, even more preferably 5 mass % or less, and may not be contained. The volatile oil agent is an oil agent having a property of volatilizing at 25° C. under atmospheric pressure, preferably an oil agent having a boiling point at atmospheric pressure of 260° C. or less, a vapor pressure at 25° C. of from 0.01 to 6 mmHg, more preferably an oil agent having a boiling point at atmospheric pressure of 260° C. or less, and a vapor pressure at 25° C. of from 0.02 to 1.5 mmHg. Examples of the volatile oil include a volatile hydrocarbon, a cyclic silicone oil, a silicone oil, and a fluorine oil.

Examples of the hydrocarbon oil include a hydrocarbon oil in a liquid state at 20° C. such as liquid paraffin, squalane, squalene, n-octane, n-heptane, cyclohexane, light isoparaffin, and liquid isoparaffin, and a hydrocarbon oil in a solid or a semi-solid state at 20° C. such as vaseline, ceresin, paraffin wax, microcrystalline wax, Ozokerite, hydrogenated polyisobutene, polyethylene wax, and polyolefin wax. One or more selected from the group consisting of liquid paraffin, liquid isoparaffin, squalane, and vaseline, are preferable from the viewpoint of impression from use.

Examples of the ester oil include an ester consisting of a linear or branched chain fatty acid and a linear or branched chain alcohol or a polyhydric alcohol, and a triglycerin fatty acid ester (triglyceride). Specific examples thereof include isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, acetylated lanolin, isocetyl stearate, isocetyl isostearate, cholesteryl 12-hydroxystearate, ethyleneglycol di(2-ethylhexanoate), dipentaerythritol fatty acid ester, N-alkylglycol monoisostearate, neopentylglycol dicaprate, diisostearyl malate, glyceryl di(2-heptylundecanoate), trimethylolpropane tri(2-ethylhexanoate), trimethylolpropane triisostearate, pentaerythritol tetra(2-ethylhexanoate), glyceryl tri(2-ethylhexanoate), trimethylolpropane triisostearate, cetyl 2-ethylhexanoate, 2-ethylhexyl palmitate, diethylhexyl naphthalenedicarboxylate, (C12-15)alkyl benzoate, cetearyl isononanoate, caprylic/capric triglyceride, dicaprylic/capric butyleneglycol, glyceryl trilaurate, glyceryl trimyristate, glyceryl tripalmitate, glyceryl triisostearate, glyceryl tri(2-heptylundecanoate), glyceryl tribehenate, glyceryl tricocoate, castor oil fatty acid methyl ester, oleyl oleate, 2-heptylundecyl palmitate, diisobutyl adipate, N-lauryol-L-glutamate-2-octyldodecyl ester, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, di(2-ethylhexyl) succinate, triethyl citrate, 2-ethylhexyl para-methoxycinnamate, and tripropylene glycol dipivalate.

Among these, from the viewpoint of adhering the coating to the skin, at least one selected from the group consisting of octyldodecyl myristate, myristyl myristate, isocetyl stearate, isocetyl isostearate, cetearyl isonanoate, diisobutyl adipate, di-2-ethylhexyl sebacate, isopropyl myristate, isopropyl palmitate, diisostearyl malate, neopentylglycol dicaprate, (C12-15)alkyl benzoate, and caprylic/capric triglyceride, is preferable. At least one selected from the group consisting of isopropyl myristate, isopropyl palmitate, diisostearyl malate, neopentylglycol dicaprate, (C12-15)alkyl benzoate, and caprylic/capric triglyceride is more preferable. It is further preferable to contain one or more selected from neopentylglycol dicaprate, (C12-15)alkyl benzoate, caprylic/capric triglyceride and isopropyl myristate.

The oil in the present invention has an HLB value of 10 or less, and preferably 8 or less. The HLB value is an index indicating the Hydrophile-Lipophile Balance, and in the present invention, the HLB value is calculated by the following equations by Oda and Teramura et al.

$$HLB = (\Sigma \text{ inorganic value} / \Sigma \text{ organic value}) \times 10$$

The ether oils include dioctyl ether. The sheet transparentizing agent of the present invention may contain an ether oil, but the content of the ether oil in the sheet transparentizing agent is preferably 20 mass % or less, more preferably 10 mass % or less, and further more preferably 3 mass % or less, and the sheet transparentizing agent may not contain an ether oil.

An animal oil and/or a vegetable oil including the above ester oil and/or the hydrocarbon oil can be used. Examples of the animal oil and/or vegetable oil include an olive oil, a jojoba oil, a macademia nut oil, a medform oil, a castor oil, a safflower oil, a sunflower oil, an avocado oil, a canola oil, a ginseng oil, a rice germ oil, and a rice bran oil.

Examples of the higher alcohol include a C12-20 higher alcohol, specifically cetyl alcohol, stearyl alcohol, isostearyl alcohol, and oleyl alcohol, and one or more selected from these can be used.

Examples of the silicone oil include dimethylpolysiloxane, dimethylcyclopolysiloxane, methylphenylpolysiloxane, and methylhydrogenpolysiloxane. From the viewpoint of improving the adhesivity of the sheet, the content of the silicone oil in the sheet transparentizing agent is preferably less than 50 mass %, more preferably 30 mass % or less, more preferably 10 mass % or less, and the sheet transparentizing agent may not contain a silicone oil.

The sheet transparentizing agent may include a surfactant, a preservative, a polyol in a liquid state at 20° C., a water-soluble polymer, an amino acid, and the like in addition to the above-mentioned oil agent. Examples of the surfactant include a nonionic surfactant, an anionic surfactant, a cationic surfactant, and the like, such as polyoxyethylene-methylpolysiloxane copolymer, poly(oxyethylene/oxypropylene)methylpolysiloxane copolymer, cross-linked polyether-modified silicone, cross-linked alkyl polyether-modified silicone, cetyl dimethicone copolyol, propylene glycol monostearate, sorbitan monooleate, glyceryl stearate, polyoxyethylene-hydrogenated castor oil, polyoxyethylene alkyl ether, sorbitan sesquioleate, and diglyceryl monooleate. From the viewpoint of pasting the sheet transparentizing agent to the skin for a long period, one or more selected from the group consisting of the nonionic surfactant and the cationic surfactant are preferable, and one or more of the nonionic surfactant are more preferable.

The surfactant preferably has an HLB value greater than 10, more preferably 12 or more.

Examples of the preservative include phenoxyethanol, methyl para-hydroxybenzoate, ethyl para-aminobenzoate, isobutyl para-hydroxybenzoate, isopropyl para-hydroxybenzoate, ethyl para-hydroxybenzoate, butyl para-hydroxybenzoate, propyl para-hydroxybenzoate, benzyl para-hydroxybenzoate, and ethylhexanediol.

Examples of the polyol in a liquid state at 20° C. include an alkylene glycol such as ethylene glycol, propylene glycol, 1,3-propanediol, and 1,3-butanediol; polyalkylene glycols such as diethylene glycol, dipropylene glycol, polyethylene glycol having a weight average molecular weight of 2,000 or less, polypropylene glycol, and the like; glycerins such as glycerin, diglycerin, triglycerin, and the like. Among these, from the viewpoint of impression from use such as smoothness upon application, ethylene glycol, propylene glycol, 1,3-butanediol, dipropylene glycol, polyethylene glycol having a weight average molecular weight of 2,000 or less, glycerin, and diglycerin are preferable, and propylene glycol, 1,3-butanediol, and glycerin are more preferable, and propylene glycol and 1,3-butanediol are further more preferable.

When polyol in a liquid state at 20° C. is contained, the total amount of the content of the sheet transparentizing agent and the polyol in a liquid state at 20° C. is preferably 15 mass % or more, more preferably 20 mass % or more, more preferably 25 mass % or more; preferably 100 mass % or less, from the viewpoint of maintaining transparency and of improving adhesivity.

Although a water-soluble polymer may be contained in the sheet transparentizing agent, the content thereof is preferably 2 mass or less, more preferably 1 mass % or less, and more preferably 0.5 mass % or less, from the viewpoint of improving adhesivity of the nanofiber sheet to the skin and of improving transparency. As such a water-soluble polymer, those confering viscosity are preferred; one or more selected from the group consisting of xanthan gum, carboxyvinyl polymer, acrylic acid/methacrylates copolymer, sodium acrylate/sodium acryloyldimethyltaurine copolymer, hydroxyethyl cellulose, hydroxypropyl cellulose, hydroxypropylmethyl cellulose are preferred.

The method for applying the sheet transparentizing agent to the skin is not particularly limited as long as it is a method other than the electrospinning method; for example, a method of applying the sheet transparentizing agent using a tool such as a finger or an applicator, and a spray are included.

The amount of the sheet transparentizing agent to be applied to the skin may be an amount necessary and sufficient to improve the adhesivity between the skin and the coating. From the viewpoint of ensuring the adhesivity between the skin and the coating, the amount of the sheet transparentizing agent to be applied to the skin is preferably such that the basis weight of the sheet transparentizing agent is 0.1 mg/cm$^2$ or more, more preferably 0.2 mg/cm$^2$ or more, further more preferably 0.4 mg/cm$^2$ or more, preferably 15 mg/cm$^2$ or less, more preferably 10 mg/cm$^2$ or less, and further from the viewpoint of keeping the sheet transparentizing agent on the skin and the nanofiber sheet on the skin surface at the time of transferring the nanofiber sheet and from the viewpoint of impression from use, preferably 7 mg/cm$^2$ or less and further more preferably 5 mg/cm$^2$ or less. For example, the amount of the sheet transparentizing agent to be applied to the skin is preferably an amount such that the basis weight is 0.1 mg/cm$^2$ or more and 15 mg/cm$^2$ or less, more preferably 0.2 mg/cm$^2$ or more and 10 mg/cm$^2$ or less, further more preferably 0.4 mg/cm$^2$ or more and 7 mg/cm$^2$ or less, and even more preferably 0.4 mg/cm$^2$ or more and 5 mg/cm$^2$ or less.

The amount of the oil agent when the sheet transparentizing agent is applied to the skin or the coating is preferably 0.2 mg/cm$^2$ or more, more preferably 0.3 mg/cm$^2$ or more, more preferably 0.4 mg/cm$^2$ or more, more preferably 10 mg/cm$^2$ or less, more preferably 7 mg/cm$^2$ or less, further more preferably 5 mg/cm$^2$ or less, from the viewpoint of improving the adhesivity between the skin and the coating and of improving the transparency. From the viewpoint of keeping the sheet transparentizing agent on the skin and the nanofiber sheet on the skin surface at the time of transferring the nanofiber sheet and from the viewpoint of impression from use, it is further preferably 4 mg/cm$^2$ or less. Specifically, it is preferably 0.2 mg/cm$^2$ or more and 10 mg/cm$^2$ or less, more preferably 0.3 mg/cm$^2$ or more and 7 mg/cm$^2$ or less, further more preferably 0.4 mg/cm$^2$ or more and 5 mg/cm$^2$ or less, and even more preferably 0.4 mg/cm$^2$ or more and 4 mg/cm$^2$ or less.

Next, Step (2) will be described.

The nanofiber sheet used in Step (2) is a white nanofiber sheet mainly composed of a water-insoluble polymer. The nanofiber sheet can be prepared by electrostatically spraying a solution containing a water-insoluble polymer and a volatile substance, also referred to as a spraying composition, onto a substrate.

The electrospinning method includes a step of electrospinning a spraying composition onto a substrate using an electrospinning device. The electrospinning device basically includes a container containing a spraying composition, a nozzle for discharging the spraying composition therefrom, a supply device for supplying the spraying composition contained in the container to the nozzle, and a power supply for applying a voltage to the nozzle.

FIG. 1 shows a device 10 for carrying out the electrospinning process described above. In order to carry out the electrospinning process, a device 10 with a syringe 11, a high-voltage source 12 and a conductive collector 13 is used. The syringe 11 includes a cylinder 11a, a piston 11b, and a capillary 11c. The inner diameter of the capillary 11c is about from 10 to 1000 μm. The cylinder 11a is filled with a solution containing a water-insoluble polymer serving as a raw material of the nanofibers and a volatile substance. The high voltage source 12 is, for example, a DC voltage source of from 10 to 30 kV. The positive electrode of the high voltage source 12 is in electrical communication with the water-soluble polymer solution in the syringe 11. The negative electrode of the high voltage source 12 is grounded. The conductive collector 13 is, for example, a metal plate and is grounded. The distance between the tip of the capillary 11c in the syringe 11 and the conductive collector 13 is set to, for example, about from 30 to 300 mm. The device 10 shown in FIG. 1 can be operated in air. The operating environment is not particularly limited, and the temperature may be from 20° C. to 40° C. and the humidity may be from 10% RH to 50% RH.

Under a state in which a voltage is applied between the syringe 11 and the conductive collector 13, the piston 11b of the syringe 11 is gradually pushed in, and the solution of the water-insoluble polymer is extruded from the tip of the capillary 11c. In the extruded solution, the solvent is volatilized, and the water-insoluble polymer (a solute), is solidified while being stretched and deformed by a potential difference to form nanofibers, which are attracted to the conductive collector 13. At this time, by disposing a sheet to be a substrate layer (not shown) on the surface of the conductive collector 13, nanofibers can be deposited on the surface of the substrate layer. The nanofibers thus formed are, continuous fibers of infinite length, in principle.

Next, a solution containing a water-insoluble polymer and a volatile substance (a spraying composition) will be described.

The volatile substance used in the spraying composition is a substance having volatility in a liquid state. In the spraying composition, the volatile substance is discharged from the nozzle tip toward the conductive collector after the spraying composition placed in the electric field is sufficiently charged, and when the volatile substance evaporates, the charge density of the spraying composition becomes excessive, and the volatile substance evaporates further while being further refined by Coulomb repulsion, and finally, the volatile substance is blended for the purpose of forming a dry coating. For this purpose, the volatile substance preferably has a vapor pressure of 0.01 kPa or more and 106.66 kPa or less, more preferably 0.13 kPa or more and 66.66 kPa or less, further more preferably 0.67 kPa or more and 40.00 kPa or less, and even more preferably 1.33 kPa or more and 40.00 kPa or less at 20° C. As the volatile substance, halogenated hydrocarbons such as chloroform, amides such as dimethylformamide, alcohols, ketones, and the like may be used.

Among the volatile substances, as the alcohol, for example, a monovalent chain aliphatic alcohol, a monovalent cyclic aliphatic alcohol, and a monovalent aromatic alcohol are suitably used. Examples of the monovalent chain aliphatic alcohol include a $C_1$-$C_6$ alcohol, examples of the monovalent cyclic alcohol include a $C_4$-$C_6$ cyclic alcohol, and examples of the monovalent aromatic alcohol include benzyl alcohol and phenylethyl alcohol. Specific examples thereof include ethanol, isopropyl alcohol, butyl alcohol, phenylethyl alcohol, n-propanol, n-pentanol, and the like. As these alcohols, one or more selected therefrom can be used.

Among the volatile substances, examples of the ketone include a $C_1$-$C_4$ dialkyl ketone, for example, acetone, methyl ethyl ketone, and methyl isobutyl ketone. These ketones can be used alone or in combination of two or more.

The volatile substance is more preferably one or more selected from the group consisting of ethanol, isopropyl alcohol and butyl alcohol, more preferably one or more selected from the group consisting of ethanol and butyl alcohol, and further more preferably ethanol.

The content of the volatile substance in the spraying composition is preferably 50 mass % or more, more preferably 55 mass % or more, further more preferably 60 mass % or more, and even more preferably 65 mass % or more. It is preferable that the content of the volatile substance be 95 mass % or less, more preferably 94 mass % or less, further more preferably 93 mass % or less, and even more preferably 92 mass % or less. The content of the volatile substance in the spraying composition is preferably 50 mass % or more and 95 mass % or less, more preferably 55 mass % or more and 94 mass % or less, further more preferably 60 mass % or more and 93 mass % or less, and even more preferably 65 mass % or more and 92 mass % or less.

As the water-insoluble polymer, a suitable polymer may be used depending on the property of the volatile substance. Specifically, water-insoluble polymers are polymers that are soluble in the volatile substance and insoluble in water. In the present specification, the term "water-insoluble polymer" means a polymer having a property that weighed 1 g of the polymer is immersed in 10 g of ion-exchange water under 1 atm at 23° C. and more than 0.5 g of the immersed polymer is undissolved after the lapse of 24 hours.

Examples of the water-insoluble polymer include fully saponified polyvinyl alcohol which can be insolubilized after the formation of a coating, a partially saponified polyvinyl alcohol which can be crosslinked in combination with a crosslinking agent, an oxazoline-modified silicone such as poly(N-propanoylethyleneimine)-graft-dimethylsiloxane/γ-aminopropylmethylsiloxane copolymer, polyvinyl acetal diethylaminoacetate, Zein (a main component of corn protein), polyester, polylactic acid (PLA), an acrylic resin such as a polyacrylonitrile resin and a polymethacrylic acid resin, a polystyrene resin, a polyvinyl butyral resin, a polyethylene terephthalate resin, polybutyrene terephthalate, a polyurerhane resin, a polyamide resin, a polyimide resin, a polyamidoimide resin, and a polypropylene resin. These water-insoluble polymers can be used alone or in combination of two or more. Among these water-insoluble polymers, one or more selected from the group consisting of completely saponified polyvinyl alcohol which can be insolubilized after film formation, partially saponified polyvinyl alcohol which can be crosslinked in combination with a crosslinking agent after the formation of a coating, an acrylic resin (e.g., a polymethacrylic acid resin), a polyvinyl butyral resin, polyurethane resin, polylactic acid, an oxazoline modified silicone such as a poly(N-propanoylethyleneimine) graft-dimethylsiloxane/γ-aminopropylmethylsiloxane copolymer, polyvinyl acetal diethylaminoacetate, and Zein can be used. Among these, from the viewpoint of strength, impression from use, adhesivity, and the like, one or more selected from the group consisting of a polyvinyl butyral resin, an acrylic resin, a polypropylene resin, polylactic acid, and a polyurethane resin are more preferable.

The content of the water-insoluble polymer in the spraying composition is preferably 1 mass % or more, more preferably 2 mass % or more, further more preferably 3 mass % or more, and even more preferably 5 mass % or more; preferably 30 mass % or less, more preferably 28 mass % or less, further more preferably 25 mass % or less, and even more preferably 23 mass % or less. The content of the water-insoluble polymer in the spraying composition is preferably 1 mass % or more and 30 mass % or less, more preferably 2 mass % or more and 28 mass % or less, further more preferably 3 mass % or more and 25 mass % or less, and even more preferably 5 mass % or more and 23 mass % or less. By containing the water-insoluble polymer in the spraying composition at this ratio, a fibrous coating can be formed in a stable and efficient manner.

The spraying composition may contain other components in addition to the above two components. Examples of the other components include a plasticizer of water-insoluble polymers, a perfume other than the above two components, a repellent, an antioxidant, a stabilizer, a preservative, and various vitamins.

The thickness of the fiber of the nanofiber sheet obtained by the electrospinning method is preferably 10 nm or more, more preferably 50 nm or more, and further more preferably 100 nm or more, when expressed as a circle equivalent diameter. The thickness is preferably 3,000 nm or less, more preferably 1,500 nm or less, and further preferably 1,200 nm or less. The thickness of the fiber can be measured by observing the fiber at a magnification of 10,000×by, for example, scanning electron microscopy (SEM) observation, removing defects (clumps of fibers, crossing portions of fibers, and droplets) from the two-dimensional image, arbitrarily selecting 10 fibers, drawing a line orthogonal to the longitudinal direction of the fiber, and directly reading the fiber diameter.

The fibers of the nanofiber sheet are continuous fibers of infinite length in principle of production, but preferably have a length of at least 100 times or more the thickness of the fibers. In the present specification, a fiber having a length of 100 times or more of the thickness of the fiber is defined as a "continuous fiber." The nanofiber sheet produced by the electrospinning method is preferably a porous discontinuous sheet composed of a deposit of continuous fibers. A sheet with such a form can be handled not only as a single sheet as an aggregate, but also has an extremely soft feature, and it is hard to separate even when a shearing force is applied, and has an advantage of excellent followability to body movement. In addition, the sheet can be advantageously easily completely removed. In contrast, a continuous sheet having no pores is not easy to peel off and has a low sweat dissipation property, leading to a blistered skin. In addition, it is difficult to completely remove a porous discontinuous sheet made of an aggregate of particles without damaging the skin, for example, an operation of applying friction or the like to the entire sheet is necessary in order to completely remove the sheet.

From the viewpoint of stackability and imparting an unnoticeable appearance, the thickness of the nanofiber sheet is preferably set to from 100 nm to 500 μm, more preferably from 500 nm to 300 μm, further more preferably from 1 μm to 100 μm, and even more preferably from 10 μm to 50 μm, in terms of stickability.

The color of the nanofiber sheet before transferring is white. The L value is preferably 80 or more, more preferably 90 or more. In addition, from the viewpoint of transparentization, the "a value" and the "b value" are each preferably from −20 to 30, more preferably from −10 to 20, and even more preferably from 0 to 10. The L value is a value determined in the CIE 1976 (L*, a*, b*) color space (CIELAB), by which 100 indicates white and 0 indicates black.

Preferably, the nanofiber sheet is prepared by electrospinning on a peelable substrate, or formed on another substrate by an electrospinning method and then laminated on a peelable substrate. Here, as the substrate, a film made of a synthetic resin such as a polyolefin resin or a polyester resin can be used.

The nanofiber sheet may be peeled from the peelable substrate and transferred onto the skin to which the sheet transparentizing agent has been applied in Step (1). Preferably, after the surface of the nanofiber sheet laminated to the peelable substrate abuts the skin, the substrate is peeled from the nanofiber sheet to transfer the nanofiber layer to the skin.

In the nanofiber sheet transferred onto the skin, the sheet transparentizing agent previously applied to the skin is uniformly distributed by the capillary phenomenon, whereby the adhesivity between the coating and the skin becomes remarkably high and the coating becomes transparent. In addition, since the coating becomes soft and easy to follow the skin, the adhesivity is further improved.

Here, on the skin, a coating in which the oil agent is uniformly distributed in the nanofiber sheet is formed. In the coating, when the volume occupied by the oil agent is $V_1$ and the void volume of the nanofiber sheet is $V_2$, $V_1/V_2$ is preferably 0.1 or more in terms of adhesivity to the skin and transparency of the coating, $V_1/V_2$ is more preferably 0.15 or more, further more preferably 0.3 or more, even more preferably 0.4 or more, even more preferably 0.5 or more, even more preferably 0.7 or more; preferably 12 or less, more preferably 10 or less, further more preferably 8 or less, and even more preferably 5 or less in terms of impression from use. $V_1/V_2$ is preferably 0.1 or more and 12 or less, more preferably 0.15 or more and 12 or less, further more preferably 0.3 or more and 10 or less, even more preferably 0.4 or more and 8 or less, even more preferably 0.5 or more and 5 or less, and even more preferably 0.7 or more and 5 or less.

Note that $V_1$ and $V_2$ are defined by the following equations, respectively.

$$V_1 = (\text{transparentizing agent and nanofiber sheet application area [cm}^2\text{]} \times \text{transparentizing agent application amount [mg/cm}^2\text{]} \times \text{oil agent content [mass \%]}) / \text{transparentizing agent density [g/cm}^3\text{]}$$

$$V_2 = \text{transparentizing agent and nanofiber sheet application area [cm}^2\text{]} \times \text{sheet film thickness [μm]} \times \text{sheet porosity [\%]}$$

Here, the oil agent content is the content of the oil agent contained in the sheet-transparentizing agent used, and the transparentizing agent density is determined by weighing the transparentizing agent in a container having a constant volume.

In addition, in the present invention, the sheet film thickness is determined by a contact-type film thickness gauge Lightmatic VL-50A manufactured by Mitsutoyo Corporation, and the porosity is determined by a mercury-injection method (AutoPorelV manufactured by Shimadzu Corporation).

The sheet porosity is preferably from 60% to 90%, more preferably from 70% to 90%, and even more preferably from 75% to 85% from the viewpoint of the sheet transparency and improving the adhesivity.

The patch material for forming a transparent or translucent coating according to the present invention is a patch material for forming a transparent or translucent coating on the skin surface, containing a sheet composed of fibers and a sheet transparentizing agent in combination. The sheet is mainly composed of a water-insoluble polymer, and the thickness of the fibers constituting the sheet is 10 nm or more and 1,500 nm or less in equivalent circle diameter, the thickness of the sheet is 100 nm to 500 μm, and the L value is 80 or more and 100 or less.

The sheet transparentizing agent contains 5 mass % or more and 100 mass % or less of an oil agent containing one or more selected from a hydrocarbon oil, an ester oil, and a higher alcohol, and the total amount P of the content of the hydrocarbon oil, the ester oil and the higher alcohol in the oil agent is 50 mass % or more.

Here, the sheet is preferably a nanofiber sheet.

For the reasons described above, the thickness of the sheet in the patch material of the present invention is preferably from 500 nm to 300 μm. It is preferable that the "a value" and the "b value" of the sheet be each from −20 to 30. The sheet preferably has a porosity of from 60% to 90%. The fibers constituting the sheet are preferably continuous fibers.

The total amount of the content of the silicone oil and the ether oil in the sheet transparentizing agent in the patch material is preferably 15 mass % or less, and the total amount of the content of the silicone oil and ether oil with respect to the total amount P is preferably 30 mass % or less.

With respect to the above embodiments, the present invention further discloses the following methods.

<1> A method for forming a coating on a skin surface using a nanofiber sheet, comprising:

(1) Step (1) of applying a sheet transparentizing agent comprising 2 mass % or more of one or more types of oil agents to the skin; and (2) Step (2) of transferring a white nanofiber sheet mainly composed of a water-insoluble polymer to the skin after Step (1).

<2> The method according to <1>, wherein, when the volume occupied by the oil agent is $V_1$ and the void volume of the nanofiber sheet is $V_2$, $V_1/V_2$ is preferably 0.1 or more, more preferably 0.15 or more, further preferably 0.3 or more, even more preferably 0.4 or more, even more preferably 0.5 or more, even more preferably 0.7 or more; preferably $V_1/V_2$ is 12 or less, more preferably $V_1/V_2$ is 10 or less, further more preferably $V_1/V_2$ is 8 or less, even more preferably $V_1/V_2$ is 5 or less, and preferably $V_1/V_2$ is 0.1 or more and 12 or less, more preferably 0.15 or more and 12 or less, further more preferably 0.3 or more and 10 or less, further more preferably 0.4 or more and 8 or less, even more preferably 0.5 or more and 5 or less, and even more preferably 0.7 or more and 5 or less.

Note that $V_1$ and $V_2$ are defined by the following equations, respectively.

$$V_1 = (\text{transparentizing agent and nanofiber sheet application area [cm}^2\text{]} \times \text{transparentizing agent application amount [mg/cm}^2\text{]} \times \text{oil agent content [mass \%]}) / \text{transparentizing agent density [g/cm}^3\text{]}$$

$$V_2 = \text{transparentizing agent and nanofiber sheet application area [cm}^2\text{]} \times \text{sheet film thickness [μm]} \times \text{sheet porosity [\%]}$$

Here, the oil agent content is the content of the oil agent contained in the sheet-transparentizing agent used, and the transparentizing agent density is determined by weighing the transparentizing agent in a container having a constant volume.

In addition, in the present invention, the sheet film thickness is determined by a contact-type film thickness gauge Lightmatic VL-50A manufactured by Mitsutoyo Corporation, and the porosity is determined by a mercury-injection method (AutoPoreIV manufactured by Shimadzu Corporation).

<3> The method according to <1> or <2>, wherein the transparentizing agent further comprises 2 mass % or less of a water-soluble polymer.

<4> The method according to any one of <1> to <3>, wherein the coating is a transparent coating through which the skin is visible.

<5> The method according to any one of <1> to <4>, wherein the content of the oil agent in the sheet transparentizing agent is 2 mass % or more, preferably 3 mass % or more, more preferably 5 mass % or more, further more preferably 8 mass % or more; preferably 100 mass % or less.

<6> The method according to any one of <1> to <5>, wherein, when the sheet transparentizing agent contains water, the content of the oil agent is preferably 3 mass % or more and 85 mass % or less, more preferably 5 mass % or more and 75 mass % or less, and further more preferably 8 mass % or more and 65 mass % or less.

<7> The method according to any one of <1> to <6>, wherein the oil agent is one or more selected from the group consisting of a hydrocarbon oil, an ester oil, a higher alcohol, an ether oil, and a silicone oil, and preferably one or more selected from the group consisting of a hydrocarbon oil, an ester oil, and a higher alcohol.

<8> The method according to any one of <1> to <7>, wherein the oil agent is one or more selected from the group consisting of a hydrocarbon oil and an ester oil.

<9> The method according to any one of <1> to <8>, wherein the content of the silicone oil and the ether oil in the sheet transparentizing agent is preferably 15 mass % or less.

<10> The method according to any one of <1> to <8>, wherein the content of the silicone oil and the ether oil in the sheet transparentizing agent is preferably 10 mass % or less.

<11> The method according to any one of <1> to <10>, wherein the oil agent in the sheet transparentizing agent comprises one or more selected from the group consisting of a hydrocarbon oil, an ester oil, and a higher alcohol, and the total amount P of the content of the hydrocarbon oil, the ester oil, and the higher alcohol is 50 mass % or more and 100 mass % or less with respect to the content of the oil agent.

<12> The method according to any one of <1> to <10>, wherein the oil agent in the sheet transparentizing agent comprises one or more selected from the group consisting of a hydrocarbon oil, an ester oil, and a higher alcohol, and the total amount S of the content of silicone oil and the ether oil to the total amount P of the content of the hydrocarbon oil, the ester oil, and the higher alcohol is preferably 30 mass % or less, more preferably 10 mass % or less.

<13> The method according to any one of <1> to <12>, wherein the sheet transparentizing agent comprises one or more selected from the group consisting of a nonionic surfactant, an anionic surfactant, a cationic surfactant, and a polyol in a liquid state at 20° C.

<14> The method according to any one of <1> to <13>, wherein the nanofiber sheet is formed by electrospinning an aqueous solution containing a water-insoluble polymer and a volatile substance.

<15> The method according to any one of <1> to <14>, wherein the thickness of the fibers of the nanofiber sheet is 10 nm or more and 3,000 nm or less, preferably 50 nm or more and 1,500 nm or less, and more preferably 100 nm or more and 1200 nm or less.

<16> The method according to any one of <1> to <15>, wherein the thickness of the nanofiber sheet is from 100 nm to 500 μm, and more preferably from 500 nm to 300 μm.

<17> The method according to any one of <1> to <16>, wherein the amount of the sheet transparentizing agent applied to the skin is such that the basis weight of the sheet transparentizing agent is preferably 0.1 mg/cm$^2$ or more, more preferably 0.2 mg/cm$^2$ or more, further more preferably 0.4 mg/cm$^2$ or more; preferably 15 mg/cm$^2$ or less, more preferably 10 mg/cm$^2$ or less, further more preferably 7 mg/cm$^2$ or less, even more preferably 5 mg/cm$^2$ or less; preferably 0.1 mg/cm$^2$ or more and 15 mg/cm$^2$ or less, more preferably 0.2 mg/cm$^2$ or more and 10 mg/cm$^2$ or less, further more preferably 0.4 mg/cm$^2$ or more and 7 mg/cm$^2$ or less, and even more preferably 0.4 mg/cm$^2$ or more and more 5 mg/cm$^2$ or less.

<18> The method according to any one of <1> to <17> wherein the amount of the oil agent when the sheet transparentizing agent is applied to the skin or to the coating, is preferably 0.2 mg/cm$^2$ or more, more preferably 0.3 mg/cm$^2$ or more, further more preferably 0.4 mg/cm$^2$ or more; preferably 10 mg/cm$^2$ or less, more preferably 7 mg/cm$^2$ or less, further more preferably 5 mg/cm$^2$ or less, even more preferably 4 mg/cm$^2$ or less; preferably 0.2 mg/cm$^2$ or more and 10 mg/cm$^2$, more preferably 0.3 mg/cm$^2$ or more and 7 mg/cm$^2$ or less, further more preferably 0.4 mg/cm$^2$ or more and 5 mg/cm$^2$ or less, and even more preferably 0.4 mg/cm$^2$ or more and 4 mg/cm$^2$ or less.

<19> The method according to any one of <1> to <18>, wherein, when the volume occupied by the oil agent is $V_1$ and the void volume of the nanofiber sheet is $V_2$, $V_1/V_2$ is 0.1 or more and 5 or less.

<20> A patch material for forming a transparent or translucent coating on the skin surface, comprising a combination of a sheet composed of fibers and a sheet transparentizing agent, wherein the sheet is mainly composed of a water-insoluble polymer, and the thickness of the fibers constituting the sheet is 10 nm or more and 1,500 nm or less in equivalent circle diameter, the thickness of the sheet is from 100 nm to 500 μm, and the L value is 80 or more and 100 or less, the sheet transparentizing agent comprises 5 mass % or more and 100 mass % or less of an oil agent comprising one or more selected from the group consisting of a hydrocarbon oil, an ester oil, and a higher alcohol, and the total amount P of the content of the hydrocarbon oil, the ester oil, and the higher alcohol in the oil agent is 50 mass % or more.

<21> The patch material for forming a transparent or translucent coating according to <20>, wherein the sheet has a thickness of from 500 nm to 300 μm.

<22> The patch material for forming a transparent or translucent coating according to <20> or <21>, wherein the sheet has "a value" and "b value" of from −20 to 30 respectively.

<23> The patch material for forming a transparent or translucent coating according to any one of <20> to <22>, wherein the total content of the silicone oil and the ether oil is 15 mass % or less.

<24> The patch material for forming a transparent or translucent coating according to any one of <20> to <23>, wherein the total amount of the content of the silicone oil and the ether oil to the total amount P is 30 mass % or less.

<25> The patch material according to any one of <20> to <24>, wherein the sheet porosity is from 60% to 90%.

<26> The patch material for forming a transparent or translucent coating according to any one of <20> to <25>, wherein the fibers constituting the sheet are continuous fibers.

EXAMPLES

The present invention will be explained in more detail by means of the following examples. However, the scope of the present invention is not limited to these examples. Unless otherwise specified, "%" means "mass %".

Test Example 1

(1) Preparation of Sheet Transparentizing Agent

The transparentizing agents 1 to 4 described in Table 1 were prepared.

Polyvinyl butyral (Sekisui Chemical Industry: Esrec B) was dissolved in ethanol to give a 15 mass % solution. This solution was used to form a nanofiber layer on the surface of a film serving as a substrate layer by the device of the electrospinning method shown in FIG. 1. The nanofibers were manufactured under the following conditions.

Applied voltage: 30 kV
Capillary-collector distance: 150 mm
Volume of aqueous solution discharged: 3 mL/h
Environment: 25° C., 30% RH The film serving as a substrate layer was a piece of polyethylene terephthalate film (25 μm thick, Taber stiffness: 0.08 mNm) coated with a silicone release processing. The nanofiber layer was formed on the surface on which release processing was given. The thickness of the nanofiber layer formed was 16 μm in Examples 1 to 6 and Comparative Examples 1 and 2, and 4.5 μm in Examples 7 to 14. The thickness of the nanofibers was 900 nm. The polypropylene resin, polymethacrylic acid resin, and urethane resin shown in Table 4 were prepared having the same thickness, fiber thickness, and porosity as in those of Example 1.

(3) Evaluation

As a skin model, black artificial leather (protein leather) (Supplare PBZ13001BK, manufactured by Idemitsu Technofine Co., Ltd.) was used, and the respective sheet transparentizing agents were applied in the amounts shown in Table 1 to the areas to which the nanofiber sheets (20 mm×40 mm) were adhered to the skin model. After the application, the nanofiber sheet was adhered, lightly pressed with a finger with a silicone glove, stored at room temperature (25° C.) and humidity (40% RH), and the state after the elapse of time was visually evaluated according to the following criteria.

TABLE 1

|  |  | Transparentizing agent | | | | | |
|---|---|---|---|---|---|---|---|
|  |  | 1 | 2 | 3 | 4 | 5 | 6 |
| A3 | Cetanol | 3.0 | 0.5 |  |  |  |  |
| A3 | Stearyl Alcohol | 2.0 | 0.5 |  |  |  |  |
| A1 | Vaseline |  | 2.0 | 100.0 |  |  |  |
| A2 | Monoglycerin fatty acid ester (*1) | 1.5 |  |  |  |  |  |
| A2 | Olive oil | 1.0 |  |  |  |  |  |
| A2 | Isopropyl myristate | 5.0 |  |  |  |  |  |
| A2 | Ester oil | 3.5 |  |  |  | 2.0 | 5.0 |
| A1 | Ceresin | 0.5 |  |  |  |  |  |
| A1 | Paraffin wax (*2) | 0.5 |  |  |  |  |  |
| A4 | Methylpolysiloxane (*5) |  | 5.0 |  |  |  |  |
|  | N-stearoyl-L-glutamic acid (*3) | 0.5 |  |  |  |  |  |
|  | Glycerol | 3.0 | 15.0 |  | 10.0 | 3.0 | 3.0 |
|  | Polyethylene Glycol (*6) |  | 3.0 |  |  |  |  |
|  | Propanediol | 3.0 |  |  |  |  |  |
|  | Dextrin Palmitate | 0.1 |  |  |  |  |  |
|  | Hydroxypropylcellulose |  | 0.25 |  |  |  |  |
|  | Arginine | 0.3 |  |  |  |  |  |
|  | Methyl Para-hydroxybenzoate |  | 0.2 |  |  |  |  |
|  | Phenoxyethanol | 0.5 |  |  |  |  |  |
|  | Na acrylate/Na acryloyldimethyltaurate copolymer | 1.13 |  |  |  | 0.38 | 0.38 |

TABLE 1-continued

|  | Transparentizing agent | | | | | |
|---|---|---|---|---|---|---|
|  | 1 | 2 | 3 | 4 | 5 | 6 |
| Polysorbate 60 |  |  |  |  | 0.21 | 0.53 |
| Purified Water | 74.47 | 73.55 | 0.0 | 90.0 | 94.41 | 91.09 |
| Total | 100.0 | 100.0 | 100.0 | 100.0 | 100.0 | 100.0 |
| Total amount of oil agent | 17.0 | 8.0 | 100.0 | 0.0 | 2.0 | 5.0 |

(*1) Sunsoft No. 8100, manufactured by Taiyo Kagaku Co., Ltd.
(*2) HNP-9, manufactured by Nippon Seiro Co., Ltd.
(*3) AmiSoft HA-P, manufactured by Ajinomoto Co., Inc.
(*4) SIMULGEL EG, manufactured by Seiwa Supply Co., Ltd.
(*5) Silicone KF-96A-10CS manufactured by Shin-Etsu Chemical Co., Ltd.
(*6) PEG-1540(-G), manufactured by Sanyo Chemical Co., Ltd.
(*7) FINSOLV TN, manufactured by Innospec Active Chemicals LLC (castor benzoate)
A1: hydrocarbon oil,
A2: ester oil,
A3: higher alcohol,
A4: silicone oil (Evaluation of Transparency)

Figure 2:
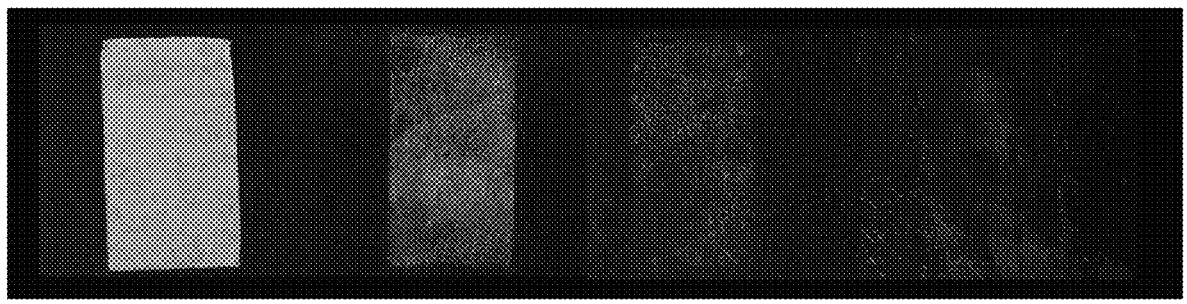
FIG. 2 shows a reference diagram of the transparency evaluation criteria.

The transparency was evaluated by the following criteria, which were visually confirmed by expert panelists (see FIG. 2).

4: Transparent and uncertain boundary with nanofiber sheet (difficult to recognize sheet application area).

3: Generally transparent, and some boundaries are visible depending on the viewing angle.

2: Coating was slightly peeled off the skin, but the entire sheet application area can be recognized.

1: Wholly the coating was peeled off the skin.

(Evaluation of Adhesivity)

Adhesivity was evaluated by the bending test of the skin model on which a coating was formed. The bending test is carried out with the condition that coatings are formed on skin models (Supplare PBZ13001BK, manufactured by Idemitsu Technofine Co., Ltd.) with the specimens angled to fold the specimens while the specimens are facing outward. In the bending test, the motion of bending the test piece was repeated 20 times with the angle of the fold in the range of 10 degrees to 180 degrees. Thereafter, the adhesivity between the coating and the skin model was visually confirmed by an expert panelist, and the adhesivity was evaluated according to the following criteria.

4: No separation or peeling off is observed between the skin model and the membrane.

3: The membrane is separated only within 10 mm from the bent portion, but the coating is not peeled off.

2: Separation of the coating occurs from the bent portion over the circumference of 10 mm, but the coating is not peeled off.

1: The coating is completely peeled off.

The evaluation results are shown in Tables 2, 3 and 4.

TABLE 2

|  | Example 1 | Example 2 | Example 3 | Comparative Example 1 | Example 4 | Example 5 | Example 6 | Comparative Example 2 |
|---|---|---|---|---|---|---|---|---|
| Fiber sheet resin | Polyvinyl butyral | Polyvinyl butyral | Polyvinyl butyral | Polyvinyl butyral | Polyvinyl butyral | Polyvinyl butyral | Polyvinyl butyral | Polyvinyl butyral |
| Transparentizing agent | 1 | 2 | 3 | 4 | 1 | 2 | 3 | 4 |
| Applied amount of transparentizing agent [mg/cm$^2$] | 3.0 | 3.0 | 3.0 | 3.0 | 5.0 | 5.0 | 5.0 | 5.0 |
| Volume of oil agent (V1) [cm$^3$] | 0.0042 | 0.0020 | 0.0267 | 0.00 | 0.0069 | 0.0033 | 0.0444 | 0.00 |
| Nanofiber void volume (V2) [cm$^3$] | 0.0102 | 0.0102 | 0.0102 | 0.0102 | 0.0102 | 0.0102 | 0.0102 | 0.0102 |
| V1/V2 | 0.41 | 0.19 | 2.62 | 0.00 | 0.68 | 0.32 | 4.37 | 0.00 |
| Transparency immediately after application | 4 | 3 |  | 2 | 4 | 4 | 4 | 4 |
| Transparency after 2 h | 4 | 3 | 4 | 1 | 4 | 3 | 4 | 1 |
| Transparency after 16 h | 4 | 2 | 4 | 1 | 4 | 3 | 4 | 1 |
| Transparency after 48 h | 4 | 1 | 4 | 1 | 4 | 2 | 4 | 1 |
| Adhesivity after 48 h | 4 | 3 | 4 | 1 | 4 | 4 | 4 | 1 |

TABLE 3

|  | Example 7 | Example 8 | Example 9 | Example 10 | Example 11 | Example 12 | Example 13 | Example 14 |
|---|---|---|---|---|---|---|---|---|
| Fiber sheet resin | Polyvinyl butyral | Polyvinyl butyral | Polyvinyl butyral | Polyvinyl butyral | Polyvinyl butyral | Polyvinyl butyral | Polyvinyl butyral | Polyvinyl butyral |

TABLE 3-continued

|  | Example 7 | Example 8 | Example 9 | Example 10 | Example 11 | Example 12 | Example 13 | Example 14 |
|---|---|---|---|---|---|---|---|---|
| Transparentizing agent | 5 | 5 | 5 | 5 | 6 | 6 | 6 | 6 |
| Applied amount of transparentizing agent [mg/cm$^2$] | 2.00 | 2.7 | 3.5 | 4.4 | 0.8 | 1.1 | 1.4 | 1.8 |
| Volume of oil agent (V1) [cm$^3$] | 0.000327 | 0.000432 | 0.000576 | 0.00072 | 0.000306 | 0.000432 | 0.000576 | 0.00072 |
| Nanofiber void volume (V2) [cm$^3$] | 0.00288 | 0.00288 | 0.00288 | 0.00288 | 0.00288 | 0.00288 | 0.00288 | 0.00288 |
| V1/V2 | 0.11 | 0.15 | 0.20 | 0.25 | 0.11 | 0.15 | 0.20 | 0.25 |
| Transparency immediately after application | 3 | 4 | 4 | 4 | 3 | 4 | 4 | 4 |
| Transparency after 2 h | 2 | 3 | 3 | 4 | 3 | 3 | 4 | 4 |
| Transparency after 16 h | 2 | 2 | 3 | 4 | 2 | 3 | 3 | 3 |
| Transparency after 48 h | 2 | 2 | 3 | 3 | 2 | 2 | 3 | 3 |
| Adhesivity after 48 h | 4 | 4 | 4 | 4 | 4 | 4 | 4 | 4 |

TABLE 4

|  | Example 1 | Example 2 | Example 3 |
|---|---|---|---|
| Fiber sheet resin | Polypropylene resin | Polymethacrylic acid resin | Polyurethane resin |
| Transparentizing agent | 1 | 1 | 1 |
| Applied amount of transparentizing agent [mg/cm$^2$] | 3.0 | 3.0 | 3.0 |
| Volume of oil substance (V1) [cm$^3$] | 0.0042 | 0.0042 | 0.0042 |
| Nanofiber void volume (V2)[cm$^3$] | 0.01 | 0.01 | 0.01 |
| V1/V2 | 0.42 | 0.42 | 0.42 |
| Transparency immediately after application | 4 | 4 | 4 |
| Transparency after 2 h | 4 | 4 | 4 |
| Transparency after 16 h | 4 | 4 | 4 |
| Transparency after 48 h | 4 | 4 | 4 |
| Adhesivity after 48 h | 4 | 4 | 4 |

EXPLANATION OF SYMBOLS

10 Electrospinning device
11 Syringe
12 High-voltage power supply
13 Conductive collector
11a Cylinder
11b Piston
11c Capillary

The invention claimed is:

1. A method for forming a coating on a skin surface using a nanofiber sheet, the method comprising:
   (1) applying to the skin a sheet transparentizing agent containing 2 mass % or more of one or more oil agent; and
   (2) transferring a white nanofiber sheet mainly composed of a water-insoluble polymer to the skin after (1), wherein the transferred white nanofiber sheet becomes transparent and the coating is a transparent coating through which the skin is visible.

2. The method according to claim 1, wherein, when the volume occupied by the oil agent is $V_1$ and the void volume of the nanofiber sheet is $V_2$, a ratio ($V_1/V_2$) is 0.1 or more.

3. The method according to claim 1, wherein the oil agent in the sheet transparentizing agent is one or more selected from the group consisting of a hydrocarbon oil, an ester oil, and a higher alcohol.

4. The method according to claim 1, wherein the sheet transparentizing agent comprises a water-soluble polymer in a content of 2 mass % or less.

5. The method according to claim 1, wherein a thickness of the fibers constituting the white nanofiber sheet is 10 nm or more and 1,500 nm or less in equivalent circle diameter, and a thickness of the white nanofiber sheet is 500 nm to 300 μm.

6. The method according to claim 1, wherein the water-insoluble polymer is one or more selected from the group consisting of a polymethacrylic acid resin, a polyvinyl butyral resin, a polypropylene resin, and a polyurethane resin.

7. The method according to claim 1, wherein the white nanofiber sheet has a porosity of from 75 to 85%.

8. The method according to claim 1, wherein the white nanofiber sheet has an "a value" and a "b value" in a range of from 0 to 10, and
   wherein an L value of the white nanofiber sheet is 90 or more and 100 or less.

9. The method according to claim 1, wherein the sheet transparentizing agent comprises 5 mass % or more and 85 mass % or less of the one or more oil agent,
   wherein the one or more oil agent is one or more selected from the group consisting of a hydrocarbon oil, an ester oil, and a higher alcohol, and
   wherein the total amount P of the content of the hydrocarbon oil, the ester oil, and the higher alcohol in the one or more oil agent is 50 mass % or more.

10. The method according to claim 1, wherein the sheet transparentizing agent contains 8 mass % or more and 65 mass % or less of the one or more oil agent.

11. The method according to claim 2, wherein the ratio $(V_1/V_2)$ is 0.4 or more and 5 or less.

12. The method according to claim 4, wherein the sheet transparentizing agent comprises a water-soluble polymer in a content of 0.5 mass % or less.

* * * * *